US012629514B2

(12) United States Patent
Bar-Tal

(10) Patent No.: US 12,629,514 B2
(45) Date of Patent: May 19, 2026

(54) BYSTANDER ATRIUM DETECTION USING CORONARY SINUS (CS) SIGNALS

(71) Applicant: BIOSENSE WEBSTER (ISRAEL) LTD., Yokneam (IL)

(72) Inventor: Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 793 days.

(21) Appl. No.: 17/734,154

(22) Filed: May 2, 2022

(65) Prior Publication Data

US 2023/0347141 A1 Nov. 2, 2023

(51) Int. Cl.
| | |
|---|---|
| *A61N 1/05* | (2006.01) |
| *A61B 5/00* | (2006.01) |
| *A61B 5/287* | (2021.01) |
| *A61B 5/346* | (2021.01) |
| *A61B 5/363* | (2021.01) |
| *A61B 5/367* | (2021.01) |

(52) U.S. Cl.
CPC ............. *A61N 1/056* (2013.01); *A61B 5/346* (2021.01); *A61N 2001/0585* (2013.01)

(58) Field of Classification Search
CPC ... A61N 1/05; A61N 2001/0585; A61B 5/346
See application file for complete search history.

(56) References Cited

U.S. PATENT DOCUMENTS

| | | | | |
|---|---|---|---|---|
| 5,755,761 A * | 5/1998 | Obino | ................... | A61N 1/056 607/9 |
| 8,521,266 B2 * | 8/2013 | Narayan | ............. | A61B 8/0883 600/515 |

| | | | |
|---|---|---|---|
| 2002/0183636 A1 | 12/2002 | Struble | |
| 2012/0172867 A1 | 7/2012 | Ryu | |
| 2021/0169359 A1 | 6/2021 | Bar-Tal | |

FOREIGN PATENT DOCUMENTS

EP 3354197 A1 * 8/2018 ............. A61B 5/339

OTHER PUBLICATIONS

International Search Report for corresponding PCT Appln. No. PCT/IB2023/054435 dated Aug. 21, 2023.
Friedman P Let al: "Inter- and intraatrial dissociation during spontaneous atrial flutter: Evidence for a focal origin of the arrhythmia", American Journal of Cardiology, Cahners Publishing Co., Newton, MA, US, vol. 50, No. 4, Oct. 1, 1982 (Oct. 1, 1982), pp. 756-761.

* cited by examiner

*Primary Examiner* — Benjamin J Klein
*Assistant Examiner* — Thien Jason Tran
(74) *Attorney, Agent, or Firm* — Scully, Scott, Murphy & Presser, P.C.

(57) ABSTRACT

An atrial flutter identification method includes placing a catheter comprising multiple electrodes in a coronary sinus (CS) of a heart of a patient, so that some of the electrodes overlap a left atrium (LA) of the heart and some of the electrodes overlap a right atrium (RA) of the heart. Intra cardiac (IC) electrophysiological (EP) signals are acquired with the electrodes. Respective signal-stability measures are estimated over the signals acquired by the electrodes overlapping the LA and over the signals acquired by the electrodes overlapping the RA. When one of the signal-stability measures is above a first threshold while the other of the signal-stability measures is below a second threshold, an atrium is indicated, that corresponds to a highest among the signal-stability measures as a source of atrial flutter.

20 Claims, 4 Drawing Sheets

BYSTANDER ATRIUM DETECTION USING CORONARY SINUS (CS) SIGNALS

FIELD OF THE DISCLOSURE

The present disclosure relates generally to electrophysiological (EP) sensing using catheters, and particularly to EP sensing of atrial flutter using catheter placed in the coronary sinus (CS).

BACKGROUND OF THE DISCLOSURE

Cardiac diagnostics and/or treatment techniques that include placing a catheter in the coronary sinus were previously proposed in the patent literature. For example, U.S. Patent Application Publication No. 2012/0172867 describes a system and method for treating an arrhythmia in a heart. The system includes positions sensors that are in contact with portions of heart tissue and analyzed changes in position are representative of motion of that tissue. The system is configured to generate an indicator, responsive to the movements of the sensors over the period of time, of a characteristic of the heart affected by delivery of ablation energy to heart tissue. In this manner, the effectiveness and safety of cardiac tissue ablation for treatment of the arrhythmia can be assessed and a post-ablation therapy regimen determined. In an exemplary embodiment, a coronary sinus (CS) catheter may also be provided for use in gathering EP data associated with the heart, to enable generation of an image of the geometry of the heart surface and related EP data. Because the coronary sinus is a relatively stable location, the CS catheter may also provide a positional reference against which positions measurements for mapping catheters are compared to compensate for cardiac motion.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
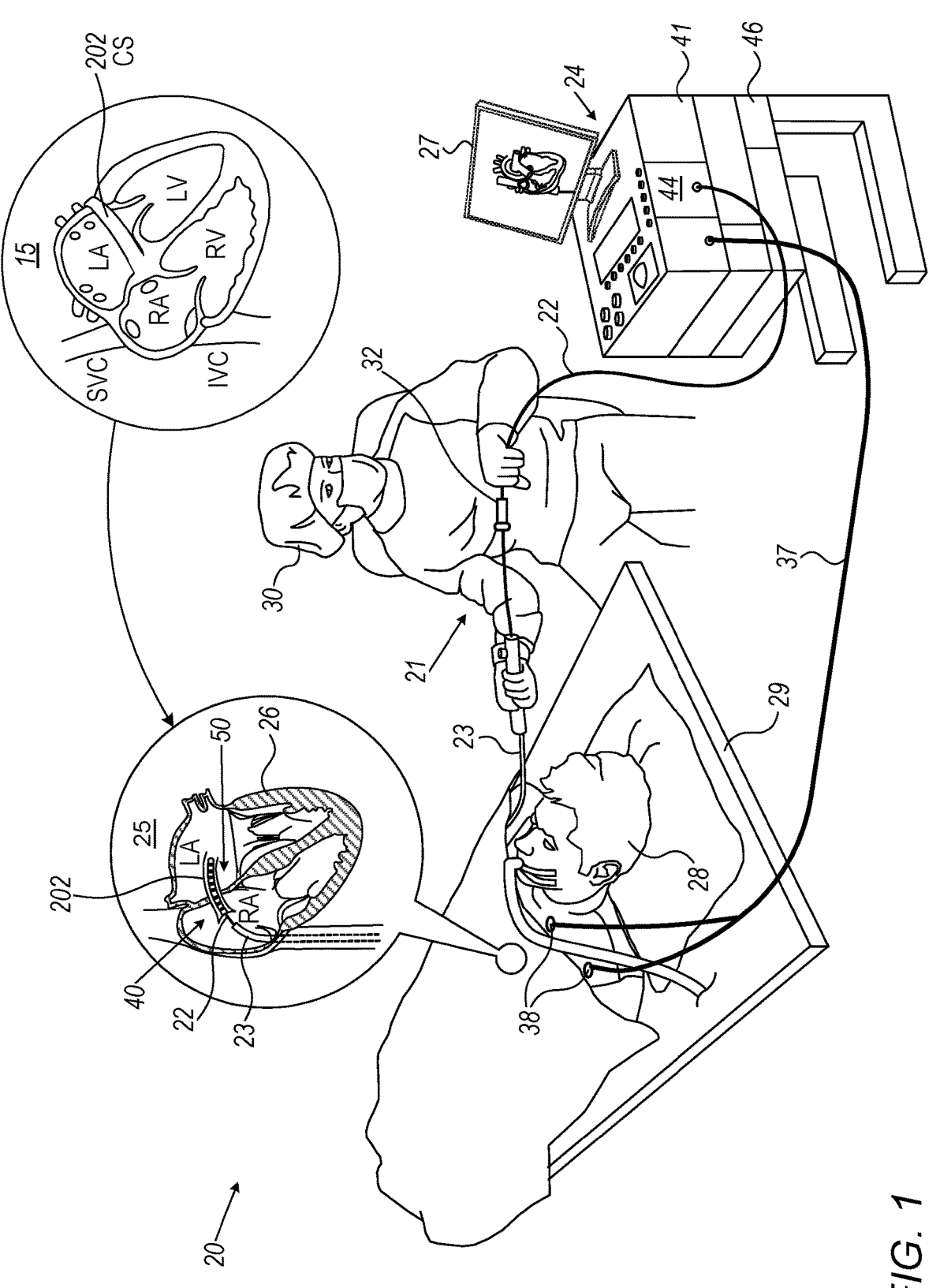
FIG. 1 is a schematic, pictorial illustration of a catheter-based electrophysiological (EP) sensing system, in accordance with an example of the present disclosure.

Atrial flutter is an abnormal heart rhythm that occurs in the atria of the heart. When it first occurs, it is usually associated with a tachycardia and falls into the category of supra-ventricular tachycardia (SVT). While this rhythm occurs most often in individuals with cardiovascular disease or diabetes it may occur spontaneously in people with otherwise normal hearts. It is typically an unstable rhythm, and frequently degenerates into atrial fibrillation. Therefore, treatment of atrial flutter is desirable.

Atrial flutter has usually been found to be caused by a single reentrant wavefront, in the left atrium (LA) or the right atrium (RA), which is characterized by continual circular activation of the atrium, usually around anatomic obstacles. Because of the reentrant nature of atrial flutter, it is often possible to ablate the circuit that causes atrial flutter. This is typically done in the electrophysiology operating theater by creating a ridge of scar tissue that crosses the path of the circuit that causes atrial flutter. Ablation of the isthmus, as discussed above, is thus a common treatment for typical atrial flutter.

When first diagnosing flutter it is not often obvious to the physician if the flutter originates in the left or right atrium. While the origin of the flutter can be determined after EP mapping of both left and right atria, it is time consuming and can also put a patient with RA flutter at risk of puncturing the septum while navigating to the LA for mapping. Moreover, if the flutter is in the RA, there may be no need to map the LA.

Examples of the present disclosure that are described herein provide a technique to acquire and analyze CS signals, captured with a CS catheter, to identify the atrium that is most likely the source of the flutter. The CS signals may be unipolar intra-cardiac (IC) electrogram (EGM) signals. The CS catheter has multiple electrodes, and is positioned so that the electrodes extend across the left and right atria including a discrete group of electrodes extending over each atrium.

Using a processor and an algorithm, the repeatability of each group of IC signals in time, (e.g., between a template of reference signals taken during a period of the arrythmia to serve as reference arrhythmogenic signal for the EP mapping), may be monitored independently and compared so that mapping will take place at periods where the heart shows the arrhythmia, thereby giving clinical value to the procedure. The atrium that is responsible for the flutter is expected to demonstrate IC signals similar to the template, while IC EGM signals from the bystander atrium are expected to be dissimilar to the reference arrhythmogenic signals.

In other words, the CS catheter with the multiple electrodes is placed so that some of the electrodes overlap the LA of the heart and some of the electrodes overlap the RA of the heart. Using EP signals from the CS catheter, the processor estimates respective signal-stability measures over the signals acquired by the electrodes overlapping the LA and over the signals acquired by the electrodes overlapping the RA. Therefore, the portion of CS signals with high signal-stability (e.g., highly correlated), either distal or proximal, is the one that with high likelihood originates from the arrhythmogenic tissue atrium.

Moreover, as a physician observes the CS signals, there is an instability of the IC CS signals at the portion of electrodes that overlaps the bystander atrium, which is due to the unstable condition of the passage of activation between the chambers. At the same time (i.e., while the arrhythmia is active), the portion of signals acquired by the CS electrodes that overlap the arrhythmogenic atrium show a high degree of repeatability (e.g., stability). Therefore, the physician can know, with a high degree of confidence, which atrium has aberrant tissue even before inserting a mapping catheter.

Typically, the processor is programmed in software containing a particular algorithm that enables the processor to conduct each of the processor-related steps and functions outlined above.

SYSTEM DESCRIPTION

FIG. 1 is a schematic, pictorial illustration of a catheter 21 based electrophysiological (EP) sensing system 20, in accordance with an example of the present disclosure. Inset 15 of FIG. 1 shows a general anatomy of a heart, and as seen, the right atrium collects deoxygenated blood from three sources, the superior vena cava (SVC), inferior vena cava (IVC), and the CS, which returns blood from the myocardium. In inset 25, catheter 21 is inserted into CS 202 to collect IC EGM signals that may indicate atrial flutter originating either from the RA or the LA.

Catheter 21 comprises a deflectable tip section 40 that is fitted at a distal end of a shaft 22 of catheter 21 with deflectable tip section 40 comprising multiple electrodes 50. In the example described herein, deflectable tip section 40 is inserted into CS 202 so that, as described in FIG. 2, a distal portion of electrodes 50 overlaps the LA of heart 26 to acquire EP signals originating in the LA, while a proximal portion of electrodes 50 overlaps the RA of heart 26 to acquire EP signals originating in the RA. The IC EGM signals may be unipolar signals, measured between electrodes 50 and surface electrodes 38, which are seen in the exemplified system as attached by wires running through a cable 37 to the chest of patient 28 lying on table 29.

The proximal end of catheter 21 is connected to a control console 24 comprising interface circuits 44. Electrodes 50 are connected by wires running through shaft 22 interface circuits 44, where the EP signals are received and processed (e.g., digitized), and output to processor 41 in console 24 for analysis.

Processor 41 may further receive electrical impedance signals measured between electrodes 50 and surface electrodes 38. A method for tracking the positions of electrodes 50 using the measured impedances is implemented in various medical applications, for example in the CARTO™ system, produced by Biosense-Webster (Irvine, California) which is described in detail in U.S. Pat. No. 8,456,182, and which is assigned to the assignee of the current disclosure. This method is sometimes called Advanced Catheter Location (ACL). Console 24 drives a display 27, which shows the tracked position and/or shape of deflectable tip section 40 inside heart 26. The various signals, such as the EP signals, are stored in a memory 46.

Processor 41, shown comprised in control console 24, is typically a general-purpose computer with suitable front end and interface circuits 44 for receiving signals from catheter 21 in a left atrium of heart 26 and for controlling the other components of system 20. Processor 41 typically comprises software in memory 46 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

Bystander Atrium Detection Using CS Signals

Figure 2:
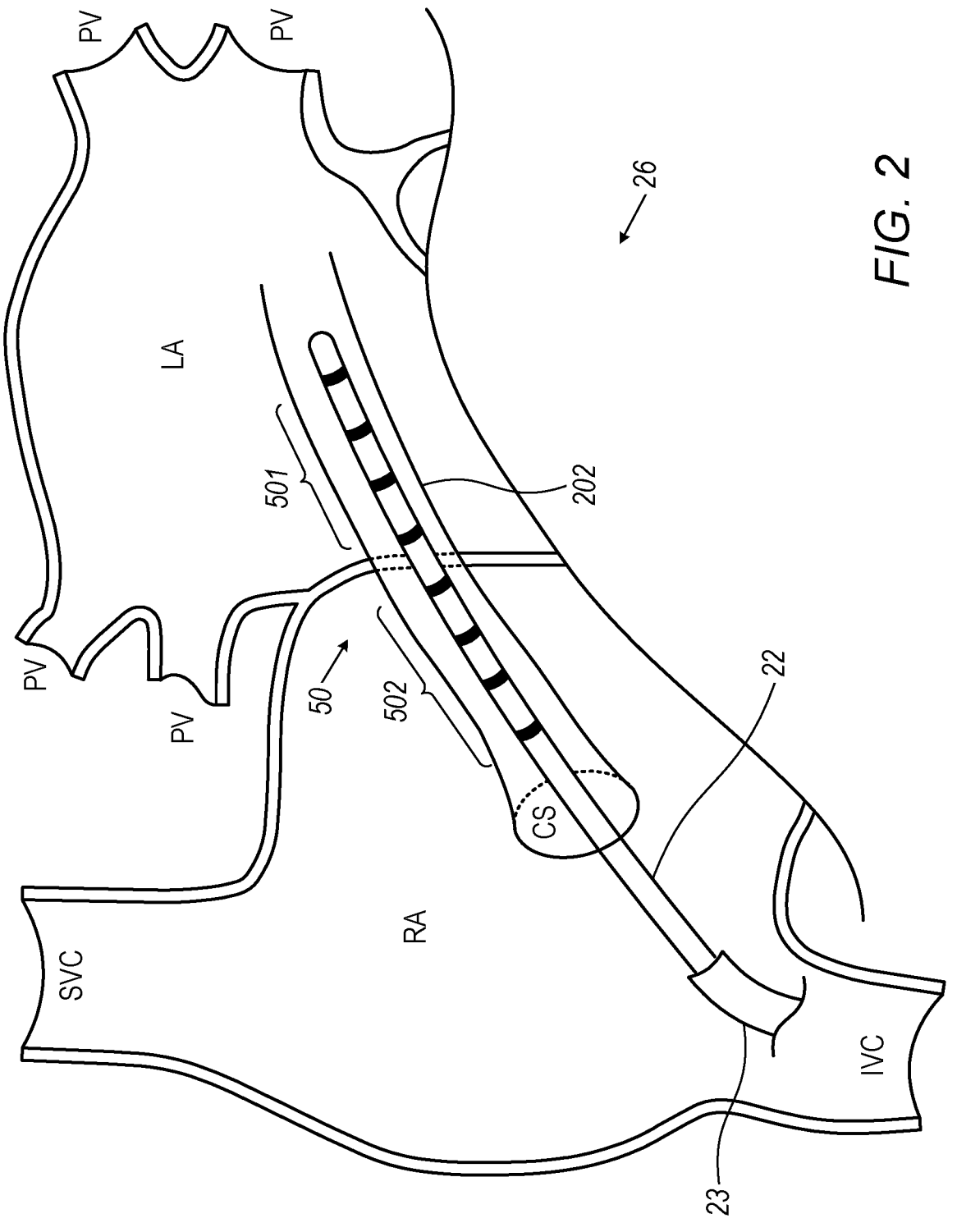
FIG. 2 is a schematic, pictorial illustration of the catheter of FIG. 1 placed in the coronary sinus (CS), in accordance with an example of the disclosure.

FIG. 2 is a schematic, pictorial illustration of the catheter 21 of FIG. 1 placed in the coronary sinus (CS), in accordance with an example of the disclosure. As seen, a distal portion 501 of electrodes 50 overlaps the LA, while a proximal portion 502 of electrodes 50 overlaps the RA. Electrodes belonging to distal portion 501 acquire local IC signals associated primarily with the LA tissue, whereas electrodes belonging to proximal portion 502 acquire local IC signals associated primarily with the LA tissue.

Figures 3A, 3B:
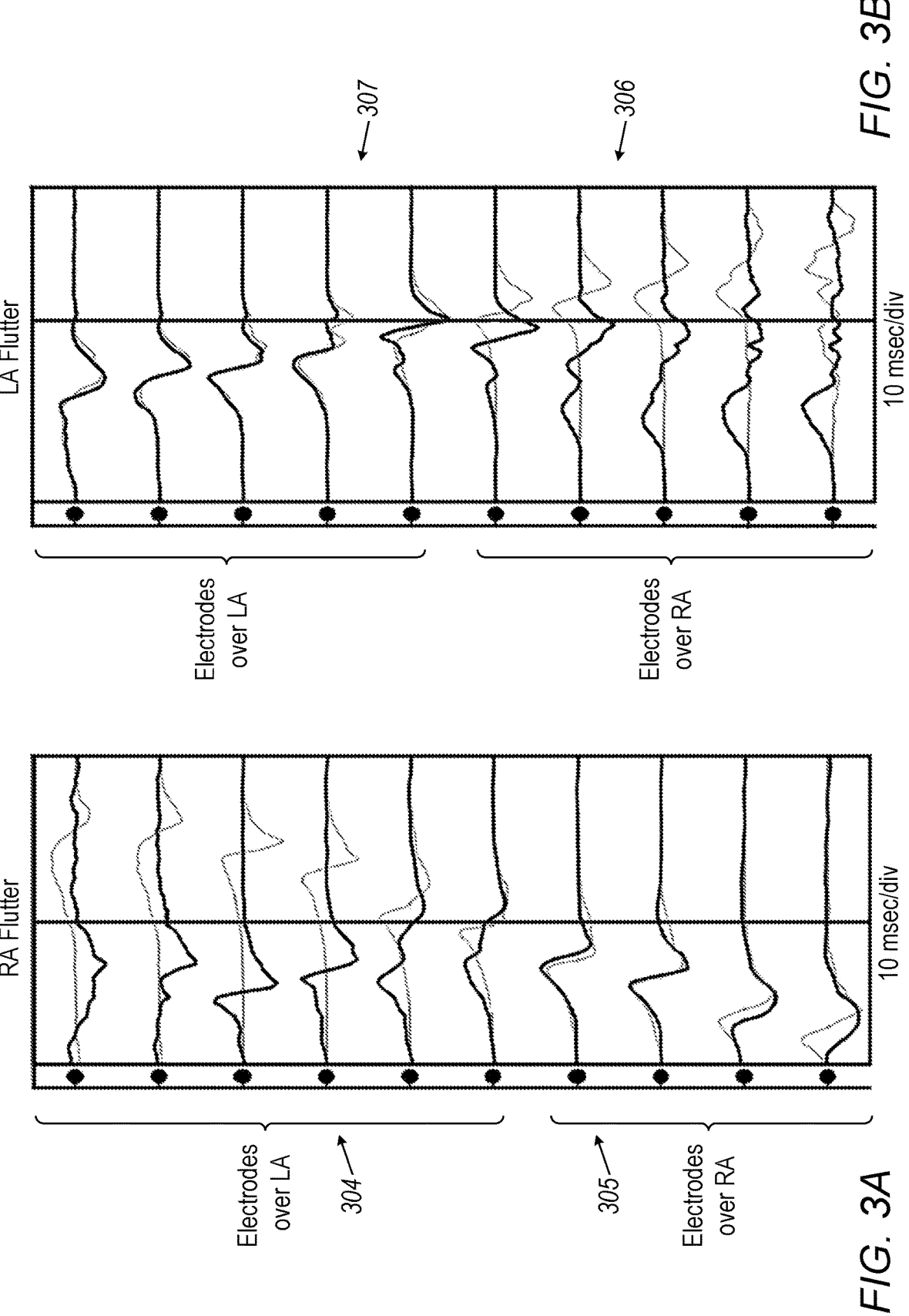
FIGS. 3A and 3B are sets of graphs of intra-cardiac EP signals from two heart cycles acquired by electrodes of the catheter of FIG. 1 placed in the CS, in accordance with an example of the disclosure.

FIGS. 3A and 3B are sets of graphs of IC EGM signals from two heart cycles acquired by electrodes of the catheter of FIG. 1 placed in the CS, in accordance with an example of the disclosure.

In FIG. 3A a distal portion 304 of the electrodes overlap the LA, whereas a proximal portion 305 of the electrodes overlap the RA. As seen, the signals from distal portion 304 are highly non-correlated (e.g., different) when comparing the template arrhythmogenic CS signal and the newly acquired one. On the other hand, the signals from proximal portion 304 are highly correlated between the two cardiac cycles. As said above, such a case is highly indicative of arial flutter origination in the RA.

As seen in FIG. 3B, which shows results from another patient, the signals from a distal portion 307 are highly non-correlated (e.g., different) when comparing the template arrhythmogenic CS signal with the newly acquired one. On the other hand, the signals from proximal portion 306 are highly correlated (e.g., similar) when comparing the two cardiac cycles. Such a case is highly indicative of arial flutter originating in the LA.

Processor 41 may quantify the above observations by calculating separate correlation scores to signals from the distal and proximal portions. In one example, stability may be determined based on such a correlation score. To this end, a method disclosed in U.S. Patent application Publication 2021/0169359, which is assigned to the assignee of the present application, may be used: a processor applies a window of interest (WOI) to the IC EGM signals representing an entire cycle length for a single heartbeat. A pattern of interest (POI) is selected to include a portion of WOI corresponding to an arrhythmia activation. A template POI is generated that is representative of the arrhythmia activation. Subsequent electrical activity is received, weights are applied, and the subsequent electrical activity is compared with the template POI. A correlation score is generated.

In the current disclosure, such correlation scores of the group of electrodes associated with the left atrium are compared to correlation scores of the group of electrodes associated with the right atrium. Based on the comparison, the atrium that is causing the flutter may be identified.

For example, processor 41 compares each portion of the correlation score to a predefined score, and, based on this comparison, may notify a user which atrium is an origin of atrial flutter.

The description above refers to the use of correlations and correlation scores, by way of example. In alternative examples, processor 41 may use any other suitable signal-stability measure for quantifying the signal stability for the group of electrodes associated with the right atrium vs. the group of electrodes associated with the left atrium.

Method of Bystander Atrium Detection Using Cs Signals

Figure 4:
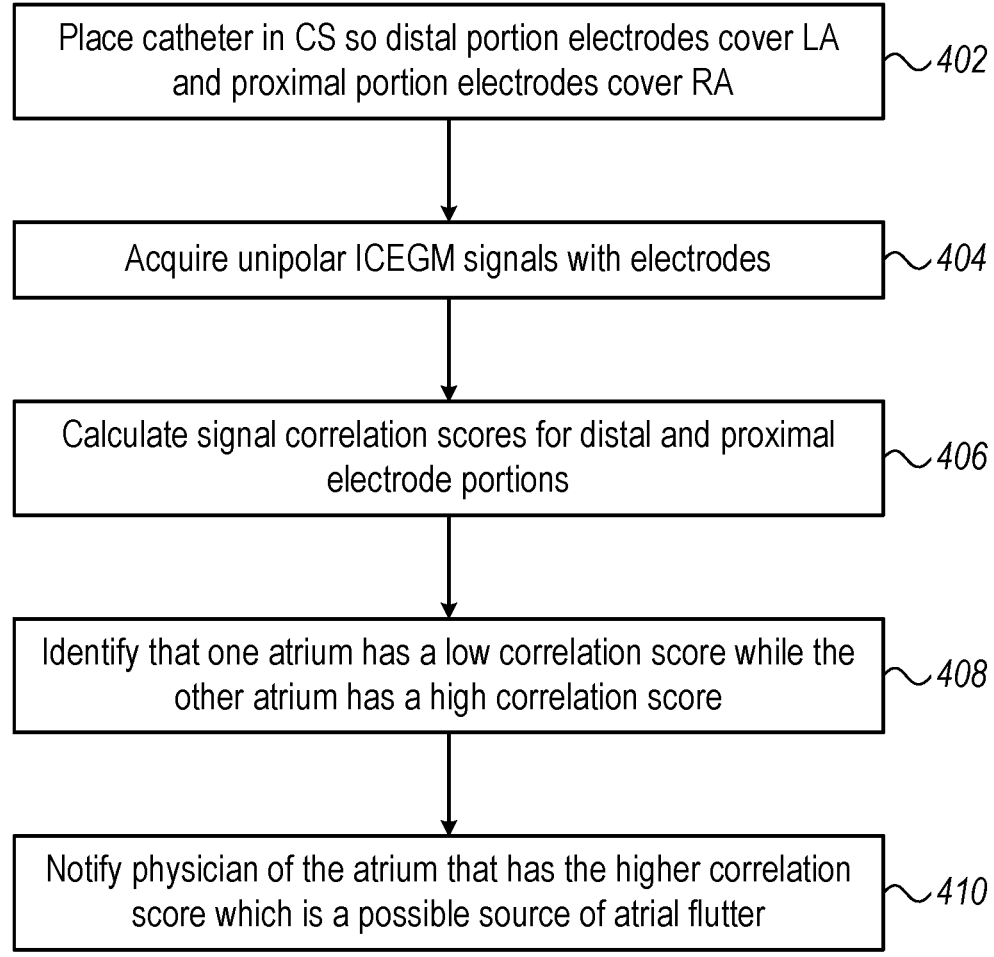
FIG. 4 is a flow chart that schematically illustrates a method for identifying an atrium of origin of atrial flutter, in accordance with an example of the disclosure.

FIG. 4 is a flow chart that schematically illustrates a method for identifying an atrium of origin of atrial flutter, in accordance with an example of the disclosure. The algorithm, according to the presented example, carries out a process that begins at a catheter placement step 402, with physician 30 inserting, navigating, and placing the catheter inside CS 202, with distal portion 501 and proximal portion 502 of electrodes 50 divided between covering the LA and the RA, respectively, as seen in FIG. 2. The physician 28 utilizes manipulator/handle 32 connected to sheath 23 in which shaft 22 is positioned to control the catheter 21.

Next, at EP signal acquisition step 404, physician 30 uses catheter 21 to acquire IC EGM signals at the SC, as described above.

At correlation score calculation step 406, processor 41 applies the aforementioned method to score the repeatability of the IC EGMS signals acquired by the distal and proximal portions of electrodes 50 in comparison to the template arrhythmogenic signal.

At scores comparison step 408, the processor identifies that one atrium has a low correlation score, the other atrium has a high correlation score.

Based on the comparison, processor 41 notifies the physician that the atrium having the high correlation score is the atria is identified as the source of atrial flutter, at a notification step 410.

For example, in step 408 above, when one of the signal-stability measures is above a first threshold while the other of the signal-stability measures is below a second threshold, the processor indicates in step 410, an atrium corresponding to a highest among the signal-stability measures as a source of atrial flutter.

The example flow chart shown in FIG. 4 is chosen purely for the sake of conceptual clarity. In alternative examples, additional steps may be performed, such as processor 41 acquiring position signals using electrodes 50, and, based on the position signals, performing one or both of adjusting placement of the catheter and verifying placement stability of the catheter, and the user visually inspecting the signals on the display.

EXAMPLES

Example 1

An atrial flutter identification method includes placing a catheter (21) comprising multiple electrodes (50) in a coronary sinus (CS) (202) of a heart (26) of a patient (28), so that some of the electrodes (50) overlap a left atrium (LA) of the heart and some of the electrodes (50) overlap a right atrium (RA) of the heart. Intra cardiac (IC) electrophysiological (EP) signals are acquired with the electrodes (50). Respective signal-stability measures are estimated over the signals acquired by the electrodes overlapping the LA and over the signals acquired by the electrodes overlapping the RA. When one of the signal-stability measures is above a first threshold while the other of the signal-stability measures is below a second threshold, an atrium is indicated, that corresponds to a highest among the signal-stability measures as a source of atrial flutter.

Example 2

The method according to example 1, wherein the signal-stability measures comprise correlation levels relative to respective reference IC signals.

Example 3

The method according to any of examples 1 and 2, wherein the reference IC signals are acquired during an arrhythmia period of the heart (26).

6

Example 4

The method according to any of examples 1 through 3, wherein the reference IC signals are template signals.

Example 5

The method according to any of examples 1 through 4, wherein the reference IC signals were acquired during a previous cardiac cycle, and wherein a correlation level below the second threshold is indicative of instability of IC signals between cardiac cycles.

Example 6

The method according to any of examples 1 through 5, wherein the electrodes (50) are arranged in a linear array along a distal end of the catheter.

Example 7

The method according to any of examples 1 through 6, and comprising acquiring position signals using the electrodes (50), and, based on the position signals, performing one or both of adjusting placement of the catheter (21) and verifying placement stability of the catheter.

Example 8

The method according to any of examples 1 through 7, wherein the IC EP signals are IC electrogram (EGM) signals.

Example 9

An atrial flutter identification system includes a catheter (21) and a processor (41). The catheter (21) comprises multiple electrodes (50), where the catheter is configured to be placed in in a coronary sinus (CS) (202) of a heart (26) of a patient (28) so that some of the electrodes overlap a left atrium (LA) of the heart and some of the electrodes overlap a right atrium (RA) of the heart. The processor is configured to (i) acquire intra cardiac (IC) electrophysiological (EP) signals with the electrodes (50), (ii) estimate respective signal-stability measures over the signals acquired by the electrodes overlapping the LA and over the signals acquired by the electrodes overlapping the RA, and (iii) when one of the signal-stability measures is above a first threshold while the other of the signal-stability measures is below a second threshold, indicate an atrium corresponding to a highest among the signal-stability measures as a source of atrial flutter.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An atrial flutter identification method, the method comprising:

placing a catheter comprising multiple electrodes in a coronary sinus (CS) of a heart of a patient, so that some of the electrodes overlap a left atrium (LA) of the heart and some of the electrodes overlap a right atrium (RA) of the heart;

acquiring intra cardiac (IC) electrophysiological (EP) signals with the electrodes overlapping the LA;

acquiring IC EP signals with the electrodes overlapping the RA;

determining LA signal-stability measures by comparing the IC EP signals acquired by the electrodes overlapping the LA with a reference arrhythmogenic CS signal;

determining RA signal-stability measures by comparing the IC EP signals acquired by the electrodes overlapping the RA with a reference arrhythmogenic CS signal; and when one of the LA or RA signal-stability measures is above a first threshold while the other of the LA or RA signal-stability measures is below a second threshold, indicating the atrium corresponding to the LA or RA signal-stability measures above the first threshold as a source of atrial flutter.

2. The method according to claim 1, wherein the signal-stability measures comprise correlation levels relative to respective reference IC signals.

3. The method according to claim 2, wherein the reference IC signals are acquired during an arrhythmia period of the heart.

4. The method according to claim 2, wherein the reference IC signals are template signals.

5. The method according to claim 2, wherein the reference IC signals were acquired during a previous cardiac cycle, and wherein a correlation level below the second threshold is indicative of instability of IC signals between cardiac cycles.

6. The method according to claim 2, wherein the correlation levels are determined by a computer processor applying a window of interest (WOI) to reference IC EP signals representing an entire cycle length for a single heartbeat; selecting a pattern of interest (POI) to include a portion of the WOI corresponding to an arrhythmia activation; generating a template POI that is representative of the arrhythmia activation; generating an LA correlation score by comparing the IC EP signals acquired by the electrodes overlapping the LA with the template POI; and generating an RA correlation score by comparing the IC EP signals acquired by the electrodes overlapping the RA with the template POI.

7. The method according to claim 1, wherein the electrodes are arranged in a linear array along a distal end of the catheter.

8. The method according to claim 1, and comprising acquiring position signals using the electrodes, and, based on the position signals, performing one or both of adjusting placement of the catheter and verifying placement stability of the catheter.

9. The method according to claim 1, wherein the IC EP signals are IC electrogram (EGM) signals.

10. The method according to claim 1, further including performing an ablation of the atrium indicated to be the source of the atrial flutter.

11. The system according to claim 1, further including using the catheter for performing an ablation of the atrium indicated to be the source of the atrial flutter.

12. An atrial flutter identification system, the system comprising:

a catheter comprising multiple electrodes, the catheter configured to be placed in in a coronary sinus (CS) of a heart of a patient so that some of the electrodes overlap a left atrium (LA) of the heart and some of the electrodes overlap a right atrium (RA) of the heart; and a processor, which is configured to:

acquire intra cardiac (IC) electrophysiological (EP) signals with the electrodes overlapping the LA;

acquire IC EP signals with the electrodes overlapping the RA;

determine LA signal-stability measures by comparing the IC EP signals acquired by the electrodes overlapping the LA with a reference arrhythmogenic CS signal;

determine RA signal-stability measures by comparing the IC EP signals acquired by the electrodes overlapping the RA with a reference arrhythmogenic CS signal; and when one of the LA or RA signal-stability measures is above a first threshold while the other of the LA or RA signal-stability measures is below a second threshold, indicate the atrium corresponding to the LA or RA signal-stability measures above the first threshold as a source of atrial flutter.

13. The system according to claim 12, wherein the signal-stability measures comprise correlation levels relative to respective reference IC signals.

14. The system according to claim 13, wherein the reference IC signals are acquired during an arrhythmia period of the heart.

15. The system according to claim 13, wherein the reference IC signals are template signals.

16. The system according to claim 13, wherein the reference IC signals were acquired during a previous cardiac cycle, and wherein a correlation level below the second threshold is indicative of instability of IC signals between cardiac cycles.

17. The system according to claim 12, wherein the electrodes are arranged in a linear array along a distal end of the catheter.

18. The system according to claim 12, wherein the processor is further configured to acquire position signals using the electrodes, and, based on the position signals, instruct performing one or both of adjusting placement of the catheter and verifying placement stability of the catheter.

19. The system according to claim 12, wherein the IC EP signals are IC electrogram (EGM) signals.

20. The system according to claim 13, wherein the correlation levels are determined by the processor applying a window of interest (WOI) to reference IC EP signals representing an entire cycle length for a single heartbeat; selecting a pattern of interest (POI) to include a portion of the WOI corresponding to an arrhythmia activation; generating a template POI that is representative of the arrhythmia activation; generating an LA correlation score by comparing the IC EP signals acquired by the electrodes overlapping the LA with the template POI; and generating an RA correlation score by comparing the IC EP signals acquired by the electrodes overlapping the RA with the template POI.

* * * * *